(12) United States Patent
Jiang et al.

(10) Patent No.: US 10,888,656 B2
(45) Date of Patent: Jan. 12, 2021

(54) SYRINGE PUMP

(71) Applicant: MEDCAPTAIN MEDICAL TECHNOLOGY. CO., LTD., Guangdong (CN)

(72) Inventors: Shendou Jiang, Guangdong (CN); Pan Hu, Guangdong (CN); Dongcen Li, Guangdong (CN); Qisong Liu, Guangdong (CN)

(73) Assignee: MEDCAPTAIN MEDICAL TECHNOLOGY. CO., LTD., Shenzhen (CN)

( * ) Notice: Subject to any disclaimer, the term of this patent is extended or adjusted under 35 U.S.C. 154(b) by 357 days.

(21) Appl. No.: 15/776,708

(22) PCT Filed: Jul. 20, 2016

(86) PCT No.: PCT/CN2016/090693
§ 371 (c)(1),
(2) Date: May 16, 2018

(87) PCT Pub. No.: WO2017/113766
PCT Pub. Date: Jul. 6, 2017

(65) Prior Publication Data
US 2018/0326145 A1 Nov. 15, 2018

(30) Foreign Application Priority Data
Dec. 31, 2015 (CN) .......................... 2015 1 1027810

(51) Int. Cl.
*A61M 5/145* (2006.01)
*A61M 5/172* (2006.01)
*A61M 5/142* (2006.01)

(52) U.S. Cl.
CPC ........ *A61M 5/1452* (2013.01); *A61M 5/1424* (2013.01); *A61M 5/1456* (2013.01);
(Continued)

(58) Field of Classification Search
CPC .. A61M 5/1452; A61M 5/1456; A61M 5/172; A61M 5/14236; A61M 5/1424;
(Continued)

(56) References Cited

U.S. PATENT DOCUMENTS 4,424,720 A   1/1984  Bucchianeri
4,544,369 A  10/1985  Skakoon et al.
(Continued)

FOREIGN PATENT DOCUMENTS

CN   201735018      *  5/2010 ............ A61M 5/145
CN   201735018 U      2/2011
(Continued)

OTHER PUBLICATIONS

International search report issued in corresponding international application No. PCT/CN2016/090693 dated Sep. 28, 2016.

*Primary Examiner* — Bhisma Mehta
*Assistant Examiner* — Rachel T. Smith
(74) *Attorney, Agent, or Firm* — Hautpman Ham, LLP

(57) ABSTRACT

A syringe pump is provided. The syringe pump includes a pump body, a control system, a transmission mechanism, and a propulsion mechanism. The transmission mechanism includes a bracket, a propulsion driving motor, a screw rod, a sliding seat, a half nut, and a clutch driving assembly. The propulsion driving motor configured to drive the screw rod to rotate, the clutch driving assembly is disposed on the sliding seat, and configured to drive the half nut and the screw rod to be engaged and disengaged from each other. The propulsion mechanism includes a connecting rod, a pushing block, a pressure sensing assembly, and a clutch switch. The pressure sensing assembly is disposed on the pushing block and configured to detect pressure of a piston (Continued)

rod of a syringe. The clutch switch is disposed on the pushing block and electrically connected to the clutch driving assembly.

14 Claims, 5 Drawing Sheets

(52) U.S. Cl.
CPC ........ *A61M 5/14236* (2013.01); *A61M 5/172* (2013.01); *A61M 5/1458* (2013.01); *A61M 2005/14506* (2013.01); *A61M 2205/332* (2013.01); *A61M 2205/3331* (2013.01)

(58) Field of Classification Search
CPC .......... A61M 2205/332; A61M 5/1458; A61M 2005/14506; A61M 2205/3331; A61M 5/145; A61M 2005/14288
See application file for complete search history.

(56) References Cited

U.S. PATENT DOCUMENTS

| | | | |
|---|---|---|---|
| 5,545,140 | A | 8/1996 | Conero et al. |
| 2009/0157003 | A1 | 6/2009 | Jones |
| 2017/0326293 | A1* | 11/2017 | Sims ................... A61M 5/1458 |

FOREIGN PATENT DOCUMENTS

| | | | | |
|---|---|---|---|---|
| CN | 102596287 | | A | 7/2012 |
| CN | 103120816 | * | | 2/2013 ............ A61M 5/142 |
| CN | 103120816 | | A | 5/2013 |
| CN | 103182113 | | A | 7/2013 |
| CN | 103977479 | | A | 8/2014 |
| CN | 105031765 | | A | 11/2015 |
| EP | 1110569 | | A2 | 6/2001 |

* cited by examiner

SYRINGE PUMP

CROSS REFERENCE TO RELATED APPLICATIONS

This application claims priority to Chinese Patent Application No. 201511027810.7, filed on Dec. 31, 2015, and entitled "SYRINGE PUMP", the disclosure of which is hereby incorporated by reference in its entirety.

TECHNICAL FIELD

The present disclosure relates to the field of medical equipment, and more particularly to a syringe pump.

BACKGROUND

A syringe pump is a kind of medical instrument that accurately, slightly, evenly and continuously pumps liquid into a human body. The syringe pump is convenient to use, and can be timed, and quantified. Speed and dosage of pumping liquid can be adjusted at any time according to state of a patient. In addition, the workload of medical staff can be reduced, the work efficiency can be improved, and the syringe pump can be accurately, safely, and effectively cooperated with the medical staff to rescue and treat patients.

The syringe pump generally includes a propulsion mechanism, a transmission mechanism, and other components. The syringe pump works as follows. A motor drives a screw rod to rotate through a deceleration device, and the screw rod drives a nut engaged with the screw rod to linearly motion along an axial direction of the screw rod. The nut is connected to the propulsion mechanism through a connecting device, and thus the propulsion mechanism, under the driving of the nut, linearly motions along the axial direction of the screw rod simultaneously, so as to push the piston rod of the syringe to inject the drug to the human body.

When a traditional syringe pump having a mechanical structure drives a propulsion mechanism to move, the operation always needs to press down a rocker mechanism by manually overcoming a mechanical elastic force. The structure of this kind of syringe pump is more complicated, it is necessary to press the rocker mechanism at all times during operation, and the operation is laborious. Furthermore, it is impossible to accurately control by manually a stopping position where the propulsion mechanism abuts the piston rod of the syringe, and thus it is easy to cause insufficient injection or over injection. In addition, it is difficult to stably control angle position of the rocker mechanism during operation, which may easily cause scraping on a half nut and a tip of screw thread of the screw rod of an inner of the syringe pump, thus resulting in abnormal wear of the screw thread, shortening the service life of the device, and reducing user experience.

For a syringe pump having an electrically controlled propulsion mechanism, speed and efficiency drove by a motor are limited. For example, when the syringe is mounted, it needs to wait for the propulsion mechanism to automatically retreat to its original position. After the syringe is mounted, the propulsion mechanism is advanced until it is pressed against the piston rod of the syringe, which will affect effectiveness of rescue and even endanger lives of patients, in the case of first aid or when it is necessary to quickly change drugs.

SUMMARY

The disclosure aims to provide a syringe pump which can automatically and manually control a propulsion mechanism, and is convenient to use.

To achieve the above objective, embodiments of the present disclosure provide a syringe pump. The syringe pump includes a pump body configured to mount a syringe, a control system, a transmission mechanism, and a propulsion mechanism.

The transmission mechanism includes a bracket, a propulsion driving motor, a screw rod, a sliding seat, a half nut, and a clutch driving assembly. The bracket is fixed in the pump body, the screw rod is axially in parallel with the syringe, and the screw rod is rotatably connected to the bracket along an axial direction of the screw rod. The propulsion driving motor is fixed on the bracket and in driving connection with the screw rod to drive the screw rod to rotate. The sliding seat is slidably disposed in the pump body along the axial direction of the syringe. The half nut is slidably disposed on the sliding seat with a sliding direction perpendicular to the axial direction of the screw rod. The clutch driving assembly is disposed on the sliding seat, and is drivingly connected with the half nut to drive the half nut to slide reciprocally, whereby the half nut is close to or away from the screw rod repeatedly.

The propulsion mechanism includes a connecting rod, a pushing block, a pressure sensing assembly, and a clutch switch. The connecting rod is axially in parallel with the syringe, and the connecting rod is slidably connected to the pump body along an axial direction of the connecting rod. The connecting rod has one end fixedly connected to the pushing block and the other end fixedly connected to the sliding seat. The pressure sensing assembly is disposed on the pushing block, to abut against a piston rod of the syringe to detect pressure of the piston rod, and the pressure sensing assembly is electrically connected to the control system. The clutch switch is disposed on the pushing block and electrically connected to the clutch driving assembly to control the clutch driving assembly to operate.

The propulsion driving motor and the clutch driving assembly are both electrically connected to the control system to operate under the control of the control system.

The clutch driving assembly includes a clutch driving motor and a clutch screw rod. The clutch driving motor is in driving connection with the clutch screw rod to drive the clutch screw rod to rotate along an axial direction of the clutch screw rod. The half nut is provided with a threaded hole, and the clutch screw rod is in threaded connection in the threaded hole.

The sliding seat is further provided with a clutch position sensor, and the clutch position sensor is electrically connected to the control system. The clutch position sensor is coupled to the half nut to detect a position of the half nut and configured to send position information to the control system.

The clutch switch is a button switch. The half nut moves away from the screw rod and is detached from the screw rod when the clutch switch is in a pressed state, and the half nut moves closer to the screw rod and is engaged with the screw rod when the clutch switch is in a released state.

The connecting rod is a hollow tubular structure.

The pressure sensing assembly includes a pressure sensor, a sliding column, and an elastic member. The pressure sensor is fixed in the pushing block. The sliding column is axially in parallel with the syringe, the sliding column is slidably connected to the pushing block along an axial direction of the sliding column, and the sliding column has one end configured to abut against the piston rod of the syringe and the other end configured to abut against the pressure sensor. The elastic member is arranged between the sliding column and the pushing block.

When the one end of the sliding column abuts against the piston rod of the syringe, the other end of the sliding column is configured to abut against the pressure sensor, and the elastic member is configured to deform and apply a force to the sliding column to make the sliding column move towards the syringe. When the one end of the sliding column is separated from the piston rod of the syringe, the sliding column is configured to move towards the syringe under the force applied by the elastic member and the other end of the sliding column is configured to be separated from the pressure sensor.

The one end of the sliding column is provided with an abutment piece configured to abut against the piston rod of the syringe, and the abutment piece is parallel to an end surface of the piston rod.

The pressure sensing assembly further includes a sliding column position sensor. The sliding column position sensor is electrically connected to the control system, arranged on the pushing block, and coupled to the sliding column to detect a position of the sliding column and configured to send position information to the control system.

When the other end of the sliding column abuts against the pressure sensor, the elastic member has an elastic force smaller than a resistance of the piston rod of the syringe and the sliding column is configured to slide into an interior of the pushing block. An outer surface of the pushing block and the piston rod of the syringe are separated with a gap therebetween. The propulsion mechanism further includes a clamping assembly configured to release or clamp the piston rod of the syringe, and the clamping assembly includes two claws disposed symmetrically and a clamping driving motor. Each claw is rotatably coupled to the pushing block, and disposed on a side surface of the pushing block towards the syringe. Each claw is provided with a gear, and the two gears are engaged with each other. The clamping driving motor is in driving connection with one of the two claws to drive the one of the two claws to rotate, whereby the two claws are far away from or close to each other. The clamping driving motor is electrically connected to the control system to operate under the control of the control system.

The clamping assembly further includes an angular displacement sensor, the angular displacement sensor having a rotating portion coupled to one of the two claws, where the rotating portion of the angular displacement sensor and the one of the two claws are configured to rotate synchronously. The angular displacement sensor is electrically connected to the control system to send angle information to the control system.

According to the syringe pump of the present disclosure, the clutch switch is pressed by a user to control the clutch driving assembly, to enable separation and engagement between the half nut and the screw rod, so that the propulsion mechanism can be manually moved to mount the syringe. The pressure sensing assembly can automatically detect whether the propulsion mechanism has moved to a suitable position, and the control module can control the propulsion driving motor and the clutch driving assembly to operate, so as to automatically move the propulsion mechanism to the suitable position. Meanwhile, manual and automatic control can be integrated to move the propulsion mechanism to the suitable position. Specifically, the clutch switch is manually pressed, to make the half nut be separated from the screw rod, and the propulsion mechanism is quickly moved to a rough position. The control system controls the propulsion driving motor to drive the propulsion mechanism to move to the suitable position according to pressure information of the pressure sensing assembly. In this way, accurate positioning can be achieved.

BRIEF DESCRIPTION OF THE DRAWINGS

In order to illustrate technical solutions of embodiments of the present disclosure more clearly, the drawings used in the description of the embodiments will be briefly described, it will be apparent that the drawings described in the following are embodiments of the present disclosure, and it will be apparent to those skilled in the art that other drawings can be obtained from the drawings without any creative work.

DETAILED DESCRIPTION OF ILLUSTRATED EMBODIMENTS

Figure 1:
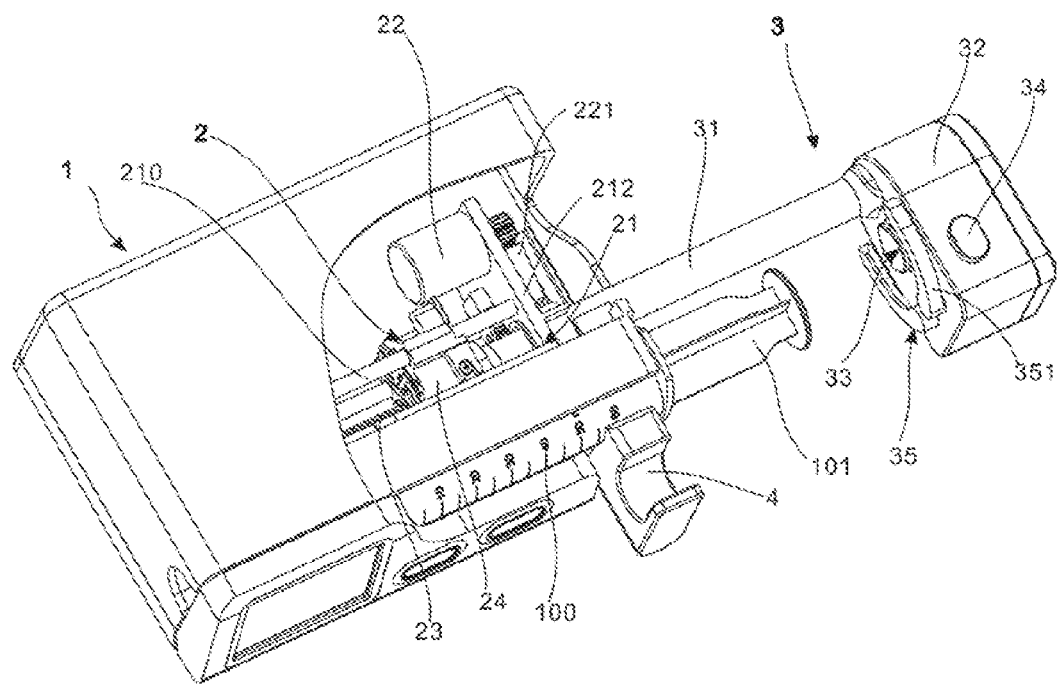
FIG. 1 is a schematic structural diagram illustrating a syringe pump according to an embodiment of the present disclosure.

In order to illustrate technical solutions of the present disclosure more clearly and completely, the present disclosure will be further described in detail below with reference to the accompanying drawings.

Referring to FIG. 1 to FIG. 5, a syringe pump is provided. The syringe pump includes a pump body 1 configured to mount a syringe 100, a control system (not shown), a transmission mechanism 2, and a propulsion mechanism 3. The control system, the transmission mechanism 2, and the propulsion mechanism 3 are disposed in the pump body 1. The propulsion mechanism 3 is configured to push a piston rod 101 of the syringe 100 to inject. The transmission mechanism 2 is configured to apply a propulsion force to the propulsion mechanism 3 to push the piston rod 101 of the syringe 100. A propulsion driving motor and a clutch driving assembly are both electrically connected to the control system to operate under the control of the control system. The control system controls the transmission mechanism 2 and the propulsion mechanism 3 to execute various instructions issued by a user.

Figure 2:
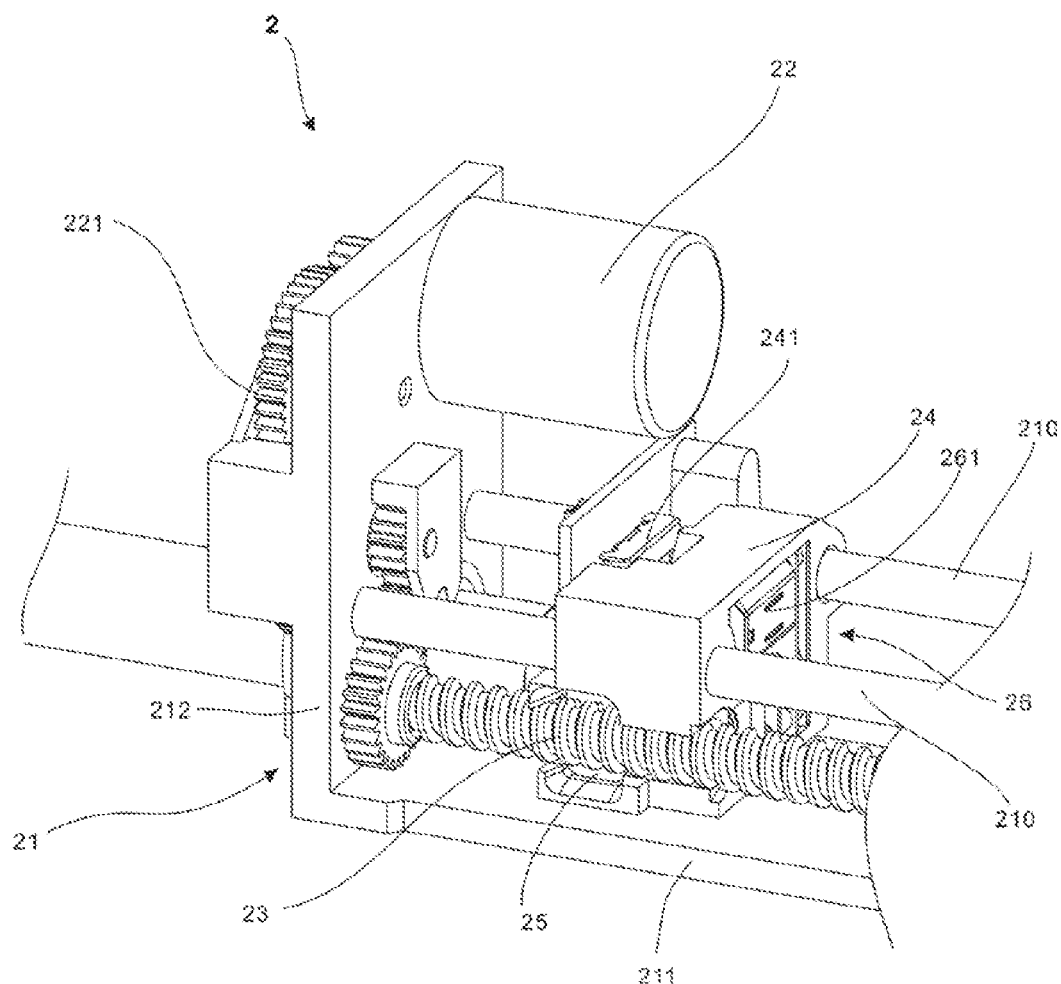
FIG. 2 illustrates a schematic structural diagram of a transmission mechanism of a syringe pump in FIG. 1.
Figure 3:
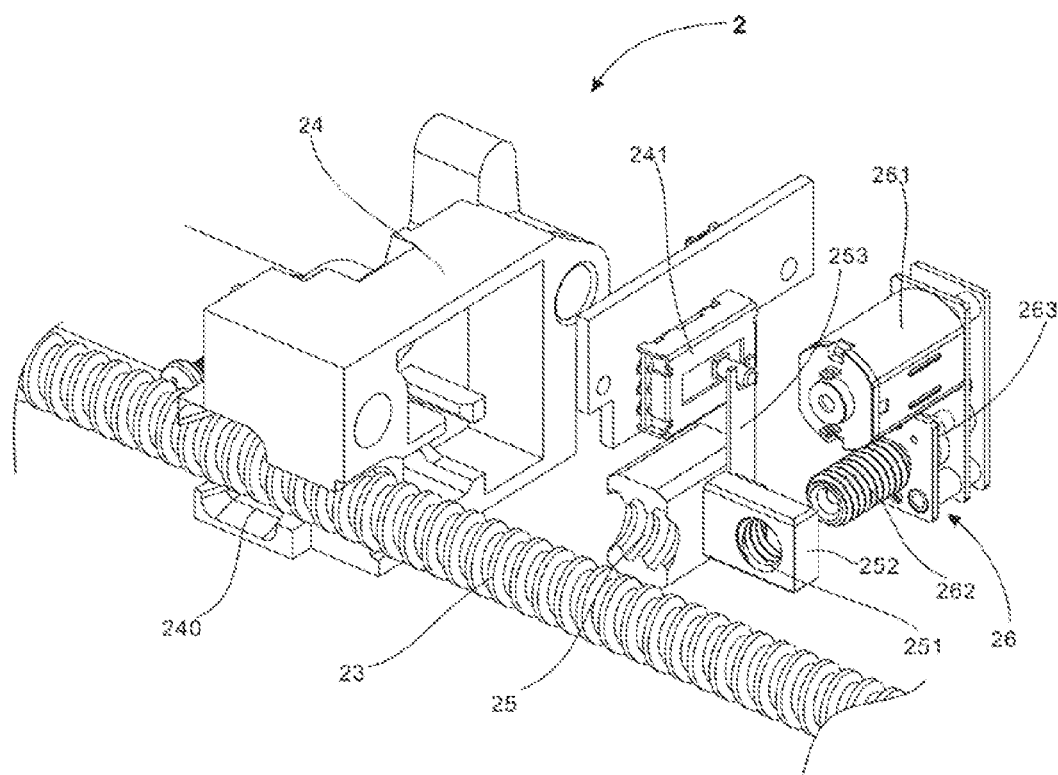
FIG. 3 illustrates a schematic exploded diagram of a transmission mechanism in FIG. 2.

As illustrated in FIG. 1 to FIG. 3, the transmission mechanism 2 includes a bracket 21, a propulsion driving motor 22, a screw rod 23, a sliding seat 24, a half nut 25, and a clutch driving assembly 26. The bracket 21 is fixed in the pump body 1. The bracket 21 is configured to support the transmission mechanism 2, and connect various parts of the transmission mechanism 2 as a whole. The propulsion driving motor 22 is disposed on the bracket 21 for driving the screw rod 23 to rotate, so as to drive the sliding seat 24 to slide. The sliding of the sliding seat 24 can drive the propulsion mechanism 3 to operate accordingly. The half nut 25 and the screw rod 23 are arranged to be separated from or close to each other. The clutch driving assembly 26 is configured to drive the half nut 25 to operate, so that the half nut 25 and the screw rod 23 can be close to or away from each other.

The screw rod 23 is axially in parallel with the syringe 100. The screw rod 23 is rotatably connected to the bracket 21 along an axial direction of the screw rod 23. The propulsion driving motor 22 is fixed on the bracket 21 and is in driving connection with the screw rod 23 to drive the screw rod 23 to rotate. In the embodiment, the propulsion driving motor 22 is drivingly connected to the screw rod 23 through a propulsion deceleration gear group 221, so that stability of rotation of the screw rod 23 can be ensured, and a rotation speed of the screw rod 23 can be precisely controlled, thereby achieving precise control of the injection. In other implementations, the propulsion driving motor 22 can also drive the screw rod 23 to rotate along the axial direction of the screw rod 23 by means of a chain transmission mechanism or a belt transmission mechanism, or by means of the propulsion driving motor 22 being directly connected to the screw rod 23.

The sliding seat 24 is slidably disposed in the pump body 1 along an axial direction of the syringe 100. The half nut 25 is slidably disposed on the sliding seat 24, and a sliding direction of the half nut 25 is perpendicular to the axial direction of the screw rod 23. The clutch driving assembly 26 is disposed on the sliding seat 24, and is in driving connection with the half nut 25 to drive the half nut 25 to slide back and forth, whereby the half nut 25 is close to or away from the screw rod 23 repeatedly.

As one implementation, the bracket 21 is provided with two guide rods 210. The two guide rods 210 are parallel to each other, and each guide rod is parallel to a sliding direction of the sliding seat 24. The sliding seat 24 is slidably disposed between the two guide rods 210. The sliding seat 24 is provided with two long holes, and each guide rod 210 penetrates through a respective long hole. With the aid of the two guide rods 210, the sliding seat 24 can reciprocate linearly along the axial direction of the screw rod 23, so that the stability of the sliding seat 24 when sliding can be ensured, and the sliding seat 24 can be slidably disposed in the pump body 1. In other implementations, the sliding seat 24 may also be slidably disposed on other components in the pump body 1. An inner wall of the pump body 1 or the bracket 21 can define a strip-shaped guide groove, so that the sliding seat 24 can be slidably disposed in the guide groove to achieve a relative sliding of the sliding seat 24 and the pump body 1.

The bracket 21 includes a bottom plate 211 and two end plates 212, where the two end plates 212 are disposed oppositely. One end plate 212 is fixed at one end of the bottom plate 211 and the other end plate 212 is fixed at the other end of the bottom plate 211. Each guide rod 210 has two ends respectively fixed to the two end plates 212. The screw rod 23 has two ends rotatably connected to the two end plates 212 to achieve a rotation connection of the screw rod 23 and the bracket 21. The propulsion driving motor 22 and the propulsion deceleration gear group 221 are disposed on the same end plate 212. The sliding seat 24 is slidably disposed between the two end plates 212 to limit a sliding range of the sliding seat 24. Thus, with the aid of the bracket 21, all parts of the transmission mechanism 2 can be connected as a whole. In addition, according to structural requirements of an interior of the pump body 1, the bracket 21 can also be made in other various structural forms.

The sliding seat 24 is provided with a groove 240. The half nut 25 is slidably disposed in the groove 240. The groove 240 can ensure the stability of the reciprocating sliding of the half nut 25. The clutch driving assembly 26 includes a clutch driving motor 261 and a clutch screw rod 262. The clutch driving motor 261 is in driving connection with the clutch screw rod 262 to drive the clutch screw rod 262 to rotate along an axial direction of the clutch screw rod 262. The half nut 25 is provided with a threaded hole 251 and the clutch screw rod 262 is threaded connection into the threaded hole 251.

When the clutch driving motor 261 rotates forwards, the half nut 25 can move linearly, along a radial direction of the screw rod 23, in a direction away from the screw rod 23, so that the half nut 25 can be disengaged from the screw rod 23. When the clutch driving motor 261 is reversed, the half nut 25 can move linearly, along the radial direction of the screw rod 23, in a direction close to the screw rod 23, so that the half nut 25 is engaged with the screw rod 23. The entire clutch driving structure is simple and easy to be assembled, and can drive the half nut 25 to move reciprocally and linearly.

The clutch driving motor 261 is in driving connection with the clutch screw rod 262 through a clutch deceleration gear group 263 to ensure stability of the rotation of the screw rod 23, thereby achieving accurate control of the movement of the half nut 25. In the embodiment, a connection block 252 is fixed on the half nut 25. The threaded hole 251 is provided on the connection block 252 to prevent the threaded hole 251 from interfering with thread on the half nut 25.

In other embodiments, the clutch screw rod 262 can be coaxially and fixedly connected with an output shaft of the clutch driving motor 261; or the clutch driving motor 261 can be in driving connection with the clutch screw rod 262 through a chain transmission mechanism, a belt transmission mechanism, and the other means. In addition, the clutch driving assembly 26 may further include the clutch driving motor 261, a gear, and a rack, where the gear and the rack are engaged with each other. The rack is fixedly connected to the half nut 25 so as to drive the half nut 25 to move along the radial direction of the screw rod 23. The clutch driving motor 261 is connected to the gear to drive the gear to rotate, so that the rack can drive the half nut 25 to move, thereby realizing separation and engagement of the half nut 25 and the screw rod 23. Alternatively, the clutch driving assembly 26 may also be a cylinder or other mechanisms that can drive the half nut 25 to perform reciprocating linear motion.

The sliding seat 24 is further provided with a clutch position sensor 241. The clutch position sensor 241 is electrically connected to the control system. The clutch position sensor 241 is connected to the half nut 25 to detect a position of the half nut 25, and thus the engaged or disengaged position of the half nut 25 can be detected in real time, and position information of the half nut 25 is sent to the control system, whereby the control system can issue a control instruction to perform the next operation. In one implementation, the half nut 25 is fixed with a paddle 253. The paddle 253 is connected to the clutch position sensor 241. The paddle 253 can facilitate a connection between the half nut 25 and the clutch position sensor 241. In other implementations, the half nut 25 may also be directly connected to the clutch position sensor 241.

Figure 4:
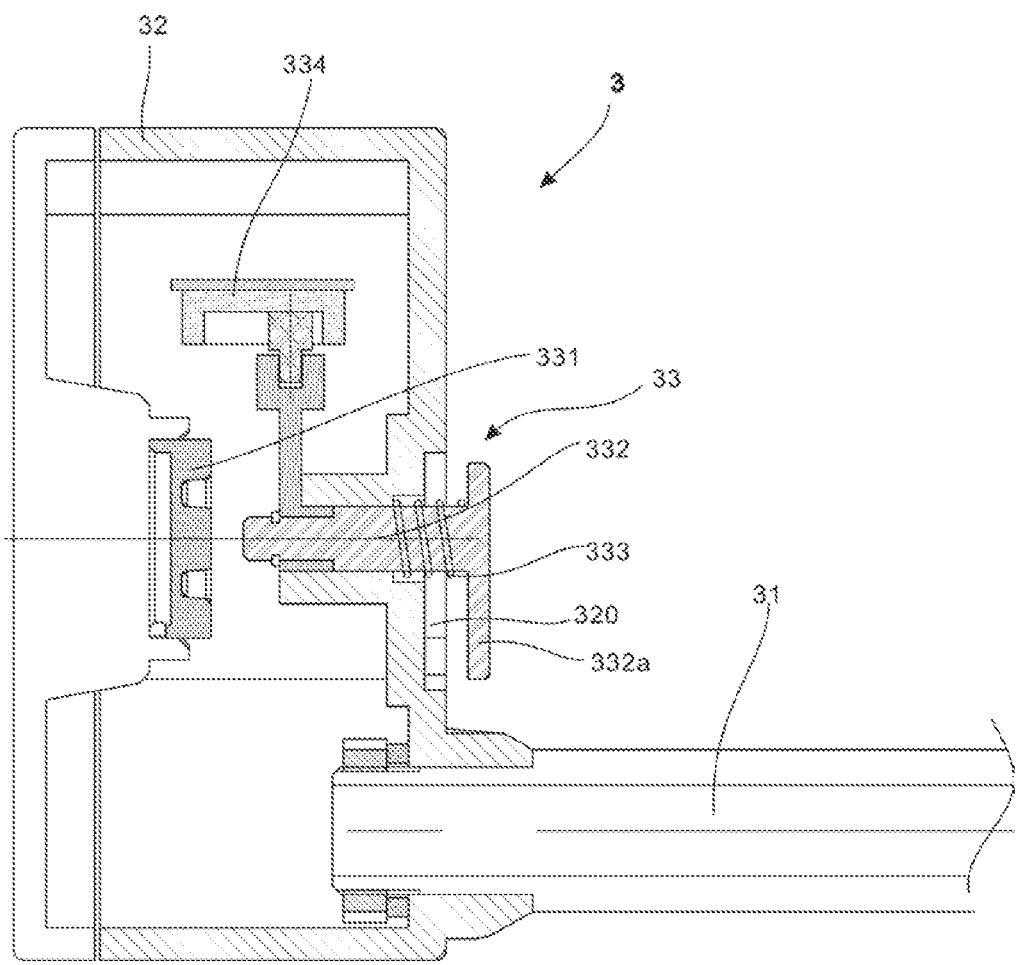
FIG. 4 illustrates a cross section of a propulsion mechanism of a syringe pump in FIG. 1.
Figure 5:
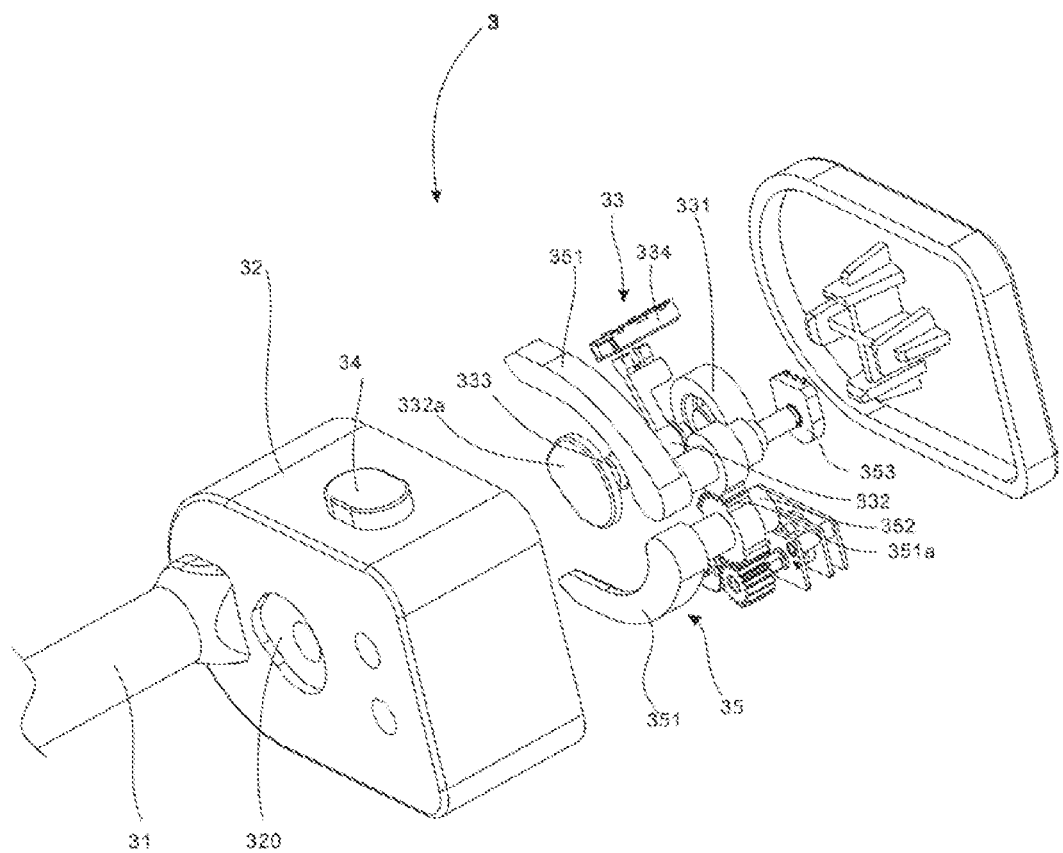
FIG. 5 illustrates a schematic exploded diagram of a propulsion mechanism of a syringe pump in FIG. 1.

As illustrated in FIG. 1, FIG. 4, and FIG. 5, the propulsion mechanism 3 includes a connecting rod 31, a pushing block 32, a pressure sensing assembly 33, and a clutch switch 34. The pressure sensing assembly 33 and the clutch switch 34 are both disposed in the pushing block 32. The pushing block 32 is fixed to the connecting rod 31. The sliding seat 24 can drive the connecting rod 31 to slide, so as to drive the pushing block 32 to move, so that the pushing block 32 can drive the piston rod 101 of the syringe 100.

The connecting rod 31 is axially in parallel with the syringe 100. The connecting rod 31 is slidably connected to the pump body 1 along an axial direction of the connecting rod 31. The connecting rod 31 has one end fixedly connected to the pushing block 32 and the other end fixedly connected to the sliding seat 24. The connecting rod 31 can slide, together with the pushing block 32, along the axial direction of the syringe 100 under the driving of the sliding seat 24.

The connecting rod 31 is a hollow tubular structure, and has connecting wires disposed inside. Electrical connections between electronic components on an inner wall of the pushing block 32 and the control system as well as electrical connections between the electronic components on the inner wall of the pushing block 32 and electronic components of the pump body 1 can be achieved with the connecting wires. The pushing block 32 is a hollow shell structure for accommodating components such as the pressure sensing assembly 33, the clutch switch 34, and the like, to facilitate assembly.

The pressure sensing assembly 33 is disposed on the pushing block 32, to abut against the piston rod 101 of the syringe 100 to detect pressure of the piston rod 101. The pressure sensing assembly 33 is electrically connected to the control system. With the abutment cooperation of the pressure sensing assembly 33 and the piston rod 101 of the syringe 100, the pressure of the piston rod 101 can be detected, and thus whether the pushing block 32 is in good contact with the syringe 100 is determined, so as to determine whether to start a normal injection. The pressure sensing assembly 33 can transmit pressure information to the control system, and then the control system sends control information to the propulsion driving motor 22 and other components, to execute corresponding operations. At the same time, in a normal injection process, the pressure sensing assembly 33 can detect injection pressure in real time to determine whether an injection channel is obstructed, to ensure normal operations of the syringe pump. When an obstruction occurs, the control system can send a prompt message to the user to facilitate the user to process timely.

In the embodiment, as illustrated in FIG. 4, the pressure sensing assembly 33 includes a pressure sensor 331, a sliding column 332, and an elastic member 333. The pressure sensor 331 is fixed in the pushing block 32. The sliding column 332 is axially parallel to the syringe 100. The sliding column 332 is slidably connected to the pushing block 32 along an axial direction of the sliding column 332. The sliding column 332 has one end configured to abut against the piston rod 101 of the syringe 100 and the other end configured to abut against the pressure sensor 331. The elastic member 333 is arranged between the sliding column 332 and the pushing block 32, to apply a force to move the sliding column 332 towards the syringe 100.

When the one end of the sliding column 332 abuts against the piston rod 101 of the syringe 100, the other end of the sliding column 332 abuts against the pressure sensor 331, and the elastic member 333 deforms and applies a force to the sliding column 332 to make the sliding column 332 move towards the syringe 100. When the one end of the sliding column 332 is separated from the piston rod 101 of the syringe 100, the sliding column 332 moves towards the syringe 100 under the force applied by the elastic member 333, and the other end of the sliding column 332 is separated from the pressure sensor 331. With the cooperation of the sliding column 332 and the pressure sensor 331, whether the propulsion mechanism 3 is installed in place with the syringe 100 is accurately detected so as to perform the next operation.

The one end of the sliding column 332 is provided with an abutment piece 332a for abutting against the piston rod 101 of the syringe 100. The abutment piece 332a is parallel to an end surface of the piston rod 101 to ensure force uniformity of the sliding column 332 and improve reliability of pressure monitoring.

In the embodiment, the elastic member 333 is a compression spring and sleeved on the sliding column 332. The elastic member 333 has one end connected to the inner wall of the pushing block 32 and the other end connected to the one end of the sliding column 332. In other implementations, the elastic member 333 may also be an elastic piece, a torsion spring, or other components that can apply an elastic force to the sliding column 332.

When the other end of the sliding column 332 abuts against the pressure sensor 331, the elastic member 333 has an elastic force smaller than a resistance of the piston rod 101 of the syringe 100. The sliding column 332 slides to an interior of the pushing block 32, and an outer surface of the pushing block 32 and the piston rod 101 of the syringe 100 are separated with a gap therebetween. Therefore, during a normal injection process, the sliding column 332 can be configured to apply a propulsion force to the piston rod 101, and the pressure sensor 331 can detect injection pressure in real time during the propulsion process, to determine whether the injection channel is obstructed. In the embodiment, since the one end of the sliding column 332 is provided with the abutment piece 332a and a recess 320 is provided on the outer surface of the pushing block 32, the abutment piece 332a can be received in the recess 320 when the outer surface of the pushing block 32 abuts against the piston rod 101 of the syringe 100. The outer surface of the abutment piece 332a protrudes from the pushing block 32 and a gap is defined between an inner surface of the abutment piece 332a and a recess bottom surface of the recess 320 when the abutment piece 332a is received in the recess 320, so that the pushing block 32 cannot be contacted with the piston rod 101 and the pushing block 32 and the piston rod 101 do not generate a direct force. Therefore the pressure sensor 331 can detect injection pressure in real time during the propulsion process.

Additionally, the pressure sensing assembly 33 further includes a sliding column position sensor 334. The sliding column position sensor 334 is electrically connected to the control system. The sliding column position sensor 334 is arranged in the pushing block 32. The sliding column position sensor 334 is coupled to the sliding column 332 for detecting a position of the sliding column 332 and sending position information to the control system, so as to detect the position of the sliding column 332 in real time. In other implementations, the pressure sensing assembly 33 may also only include a pressure sensor 331 disposed on an outer surface of the pushing block 32 towards the syringe 100, and the pressure sensor 331 directly abuts against the piston rod 101 of the syringe 100, to detect whether the syringe 100 is installed in place.

As illustrated in FIG. 1 and FIG. 5, the clutch switch 34 is disposed on the pushing block 32 and electrically connected to the clutch driving assembly 26, to control the clutch driving assembly 26 to operate. In the embodiment, the clutch switch 34 is a button switch. When the clutch switch 34 is in a pressed state, the half nut 25 moves away from the screw rod 23 and disengages from the screw rod 23. When the clutch switch 34 is in a released state, the half nut 25 moves towards the screw rod 23 and engages with the screw rod 23. After a user presses the clutch switch 34, the clutch driving motor 261 can be activated to make the half nut 25 be disengaged from the screw rod 23, and the user can slide the propulsion mechanism 3 by himself/herself to make the propulsion mechanism 3 abut against the syringe 100.

After the user releases the clutch switch 34, the clutch driving motor 261 can make the half nut 25 automatically engage with the screw rod 23, and the propulsion mechanism 3 can slide under the action of the transmission mechanism 2, to facilitate the user to use. In other embodiments, the clutch switch 34 may also be another type of switch such as a rotary switch, a touch switch, and the like. The clutch switch 34 may be directly and electrically connected to the clutch driving motor 261; or the clutch switch 34 may be electrically connected to the clutch driving motor 261 through the control system, and perform corresponding operations to the clutch driving motor 261 through the control system.

The propulsion mechanism 3 further includes a clamping assembly 35. The clamping assembly 35 is configured to release or clamp the piston rod 101 of the syringe 100. The clamping assembly 35 includes two claws 351 disposed symmetrically and a clamping driving motor 352. Each of the claws 351 is rotatably coupled to the pushing block 32. Each of the claws 351 is disposed at a side surface of the pushing block 32 facing the syringe 100. Each claw 351 is provided with a gear 351a, and the two gears 351a corresponding to the claws 351 are engaged with each other. The clamping driving motor 352 is drivingly connected to one of the claws 351 to drive the one of the claws 351 to rotate, so that the two claws 351 can be far away from or close to each other, to release or clamp the piston rod 101 of the syringe 100. The clamping driving motor 352 is electrically connected to the control system to operate under the control of the control system. The control system controls the one of the claws 351 to open or close by controlling the clamping driving motor 352 to rotate forwards or reverse, so as to release or clamp the piston rod 101 of the syringe 100.

The clamping assembly 35 further includes an angular displacement sensor 353. The angular displacement sensor 353 has a rotating portion coupled to the one of the claws 351. In addition, the rotating portion of the angular displacement sensor 353 together with the one of the claws rotates synchronously, to detect a rotation angle of the one of the claws 351 in real time. The angular displacement sensor 353 is electrically connected to the control system to send angle information to the control system so that the control system can acquire a state of the one of the claws 351 in real time.

Additionally, the syringe pump further includes a plunger mechanism 4. The plunger mechanism 4 is disposed on the pump body 1 and electrically connected to the control system, to: press-fit the syringe 100 to the pump body 1, identify specification of the syringe 100, and transmit the specification of the syringe 100 to the control system simultaneously, so that the control system can control propulsion speed of the propulsion mechanism 3.

The control system can be a central processor (CPU), and so on. The control system may have a man-machine interaction module and a control module. The man-machine interaction module is configured to enter various instructions and parameters by a user, as well as display various parameters and states of the syringe pump, etc. The control module is configured to control the syringe pump to execute various instructions entered by the user.

According to the syringe pump of the present disclosure, the propulsion mechanism 3 can be moved through three control modes: an automatic mode, a manual mode, and a semi-automatic mode. The three control modes will be described in following respectively.

The control mode for moving the propulsion mechanism 3 in the automatic mode is as follows. A control instruction for mounting the syringe 100 is sent by a user to the control system. In the embodiment, the instruction can be sent to the control system by clicking an icon, on a touch screen which is set on the pump body 1, of mounting the syringe 100. In addition, it is also possible to send the instruction to the control system by providing a key switch on the pump body 1. After the control system receives the instruction, the control system controls the propulsion driving motor 22 to reverse, and the propulsion driving motor 22 drives the screw rod 23 to rotate along the axial direction of the screw rod 23. The screw rod 23 drives the half nut 25 and the sliding seat 24 to move to the right along the axial direction of the screw rod 23, the propulsion driving motor 22 continues rotating until the propulsion mechanism 3 is driven to move to the right to a maximum position. The plunger mechanism 4 is configured to press-fit the syringe 100 on the syringe pump when the user mounts the syringe 100. Injection parameters are set and an activate key on the touch screen is clicked to send an activation command to the control system. The propulsion driving motor 22 rotates forwards. The screw rod 23 drives the half nut 25 and the sliding seat 24 to move to the left along the axial direction of the screw rod 23. The sliding seat 24 together with the propulsion mechanism 3 moves to the left at the same time until the sliding column 332 abuts against the piston rod 101 of the syringe 100 and rearwardly against the pressure sensor 331. The propulsion driving motor 22 continues rotating until the pressure sensor 331 receives a signal. The clamping driving motor 352 is reversed, the two claws 351 close and clamp the piston rod 101 of the syringe 100, and then the injection begins.

The control mode for moving the propulsion mechanism 3 in the manual mode is as follows. The clutch switch 34 on the propulsion mechanism 3 is pressed, the control system controls the clutch driving motor 261 to rotate forwards, and the clutch driving motor 261 drives the half nut 25 to be disengaged from the screw rod 23. Movement position of the half nut 25 is detected by a position sensor, and the clutch driving motor 261 continues rotating until the half nut 25 moves to a set position. The propulsion mechanism 3 is pulled by a hand of the user to the rightmost end or a position where the piston rod 101 of the syringe 100 can avoid, then the clutch switch 34 is released, and the clutch driving motor 261 is reversed and the half nut 25 is engaged with the screw rod 23 again. The syringe 100 is mounted and press-fitted onto the syringe pump with the plunger mechanism 4. The clutch switch 34 is pressed again, and then the half nut 25 is disengaged from the screw rod 23. The propulsion mechanism 3 is pushed by a hand of the user until the sliding column 332 abuts against a pusher sheet of the syringe 100, and the sliding column 332 is moved backwards to abut against the pressure sensor 331. The clutch switch 34 is released, and the control system controls the clutch driving motor 261 and the clamping driving motor 352 to reverse. The clutch driving motor 261 drives the half nut 25 to be engaged with the screw rod 23, and the clamping driving motor 352 drives the two claws 351 to be closed until the two claws 351 clamp the piston rod 101 of the syringe 100. After the syringe 100 is mounted, the injection can be started.

Since there is an error in a stopping position when manually moving the propulsion mechanism 3, the propulsion mechanism 3 may just reach, not reach, or move beyond a desired stopping position. When the propulsion mechanism 3 is not reach the desired stopping position (e.g., the propulsion mechanism 3 is not reach the desired stopping position due to release of a clutch control key when the sliding column 332 has not abutted against the piston rod 101 of the syringe 100), due to the release of the clutch control key, the control system controls the clutch driving motor 261 to reverse and the half nut 25 is engaged with the screw rod 23. Since the sliding column 332 has not abutted against the pressure sensor 331, there is no change in signal of the pressure sensor 331. At this time, since the pressure sensor 331 does not detect the pressure change, if the syringe pump is still started to perform injection, the control system will determine there has an excessive error on a starting position of the propulsion mechanism 3. Then the control system controls the propulsion driving motor 22 to rotate forwards, so that the transmission mechanism 2 drives the propulsion mechanism 3 to automatically move forward at a set speed until the pressure sensor 331 receives a signal. At this time, when the control system determines that the position of the propulsion mechanism 3 is appropriate, the clamping driving motor 352 is reversed, the two claws 351 clamp the piston rod 101 of the syringe 100, and then the injection is started. The above control process can effectively prevent an empty injection in the initial stage of the injection process of the conventional syringe pump, and therefore the injection precision is more accurate. For example, when the propulsion mechanism 3 is manually pushed beyond a desired stopping position, an overdose injection will be caused. Therefore, if the propulsion mechanism 3 is manually pushed beyond a desired stopping position, when the sliding column 332 abuts against the pressure sensor 331 and the signal of the pressure sensor 331 changes, even if the system controls the clutch driving motor 261 to reverse and the half nut 25 is engaged with the screw rod 23, it is impossible to continue to push the propulsion mechanism 3 forward at this time, and thus over injection can be effectively avoided.

According to the above two control methods, a semi-automatic control method can also be used. After the syringe 100 is mounted, the propulsion mechanism 3 is rapidly moved through a manual operation, to a position close to the pusher sheet of the syringe 100 to start the injection. Since at this time, the pusher sheet has not abutted against the piston rod 101 of the syringe 100 and the signal of the pressure sensor 331 has not been changed, the control system will control the propulsion driving motor 22 to rotate forwards and the transmission mechanism 2 drives the propulsion mechanism 3 to automatically move forward at a set speed until the pressure sensor 331 receives a signal. At this time, the control system determines that the propulsion mechanism 3 has reached desired stopping position, the clamping driving motor 352 is reversed, the two claws 351 clamp the piston rod 101 of the syringe 100, and then the injection is automatically started at a speed set by the user. Therefore, underdose injection or overdose injection caused by operating the conventional syringe pump can be effectively avoided with such a control method, and the use requirements for the operator can also be greatly reduced.

The foregoing embodiments are not intended to limit the protection scope of the technical solution. Any modifications, equivalent replacements, or improvements made thereto without departing from the spirits and principles of the disclosure shall all be encompassed within the protection of the disclosure.

What is claimed is:

1. A syringe pump, being operable in a manual operation mode and an electric operation mode, comprising:
   a pump body configured to mount a syringe;
   a control system;
   a transmission mechanism; and
   a propulsion mechanism;
   wherein the transmission mechanism comprises a bracket, a propulsion driving motor, a screw rod, a sliding seat, a half nut, and a clutch driving assembly; wherein the bracket is fixed in the pump body, the screw rod is axially in parallel with the syringe, and the screw rod is rotatably connected to the bracket along an axial direction of the screw rod; wherein the propulsion driving motor is fixed on the bracket and is in driving connection with the screw rod to drive the screw rod to rotate; wherein the sliding seat is slidably disposed in the pump body along an axial direction of the syringe; wherein the half nut is slidably disposed on the sliding seat with a sliding direction perpendicular to the axial direction of the screw rod; wherein the clutch driving assembly is disposed on the sliding seat and is in driving connection with the half nut to drive the half nut to slide reciprocally, whereby the half nut is close to or away from the screw rod repeatedly;
   wherein the propulsion mechanism comprises a connecting rod, a pushing block, a pressure sensing assembly, and a clutch switch; wherein the connecting rod is axially in parallel with the syringe, and the connecting rod is slidably connected to the pump body along an axial direction of the connecting rod; wherein the connecting rod has a first end fixedly connected to the pushing block and a second end fixedly connected to the sliding seat; wherein the pressure sensing assembly is disposed on the pushing block, to abut against a piston rod of the syringe to detect pressure of the piston rod, and the pressure sensing assembly is electrically connected to the control system; wherein the clutch switch is disposed on the pushing block and electrically connected to the clutch driving assembly to control operation of the clutch driving assembly; and
   wherein the propulsion driving motor and the clutch driving assembly are both electrically connected to the control system to enable the manual operation mode or the electric operation mode under control of the control system;
   wherein the clutch driving assembly comprises a clutch driving motor and a clutch screw rod, the clutch driving motor being in driving connection with the clutch screw rod to drive the clutch screw rod to rotate along an axial direction of the clutch screw rod, and the half nut is provided with a threaded hole, wherein the clutch screw rod is in threaded connection in the threaded hole.

2. The syringe pump of claim 1, wherein the sliding seat is provided with a clutch position sensor, and the clutch position sensor being electrically connected to the control system; wherein the clutch position sensor is coupled to the half nut to detect a position of the half nut and configured to send position information to the control system.

3. The syringe pump of claim 2, wherein the half nut is fixed with a paddle, and the paddle is connected to the clutch position sensor.

4. The syringe pump of claim 2, wherein the sliding seat is further provided with a groove, and the half nut is slidably disposed in the groove.

5. The syringe pump of claim 1, wherein the clutch switch is a button switch; wherein the half nut moves away from the screw rod and is detached from the screw rod when the clutch switch is in a pressed state, and the half nut moves close to the screw rod and is engaged with the screw rod when the clutch switch is in a released state.

6. The syringe pump of claim 1, wherein the pressure sensing assembly comprises a pressure sensor, a sliding column, and an elastic member;
- wherein the pressure sensor is fixed in the pushing block; wherein the sliding column is axially in parallel with the syringe, the sliding column is slidably connected to the pushing block along an axial direction of the sliding column, and the sliding column has a first end configured to abut against the piston rod of the syringe and a second end configured to abut against the pressure sensor; wherein the elastic member is arranged between the sliding column and the pushing block; and
- wherein the second end of the sliding column is configured to abut against the pressure sensor, and the elastic member is configured to deform and apply a force to the sliding column to make the sliding column move towards the syringe, when the first end of the sliding column abuts against the piston rod of the syringe; wherein the sliding column is configured to move towards the syringe under the force applied by the elastic member, and the second end of the sliding column is configured to be separated from the pressure sensor, when the first end of the sliding column is separated from the piston rod of the syringe.

7. The syringe pump of claim 6, wherein the first end of the sliding column is provided with an abutment piece configured to abut against the piston rod of the syringe, and the abutment piece is parallel to an end surface of the piston rod.

8. The syringe pump of claim 6, wherein the pressure sensing assembly further comprises a sliding column position sensor; wherein the sliding column position sensor is electrically connected to the control system arranged in the pushing block; coupled to the sliding column to detect a position of the sliding column; and configured to send position information to the control system.

9. The syringe pump of claim 6, wherein the elastic member has an elastic force smaller than a resistance of the piston rod of the syringe and the sliding column is configured to slide into an interior of the pushing block, when the second end of the sliding column abuts against the pressure sensor; and wherein an outer surface of the pushing block and the piston rod of the syringe are separated with a gap therebetween.

10. The syringe pump of claim 1, wherein the propulsion mechanism further comprises a clamping assembly configured to release or clamp the piston rod of the syringe, the clamping assembly comprising a first claw and a second claw disposed symmetrically and comprising a clamping driving motor; wherein each claw is rotatably coupled to the pushing block, and disposed on a side surface of the pushing block towards the syringe; wherein each claw is provided with a gear, and the two gears are engaged with each other; wherein the clamping driving motor is in driving connection with the first claw to drive the first claw to rotate, whereby the two claws are far away from or close to each other; and wherein the clamping driving motor is electrically connected to the control system to operate under the control of the control system.

11. The syringe pump of claim 10, wherein the clamping assembly further comprises an angular displacement sensor, the angular displacement sensor having a rotating portion coupled to the second claw, and the rotating portion of the angular displacement sensor and the second claw being configured to rotate synchronously; wherein the angular displacement sensor is electrically connected to the control system to send angle information to the control system.

12. The syringe pump of claim 1, further comprising:
a plunger mechanism;
wherein the plunger mechanism is disposed on the pump body and electrically connected to the control system.

13. A syringe pump, being operable in a manual operation mode and an electric operation mode, comprising:
a pump body configured to mount a syringe;
a control system;
a transmission mechanism; and
a propulsion mechanism;
wherein the transmission mechanism comprises a bracket, a propulsion driving motor, a screw rod, a sliding seat, a half nut, and a clutch driving assembly; wherein the bracket is fixed in the pump body, the screw rod is axially in parallel with the syringe, and the screw rod is rotatably connected to the bracket along an axial direction of the screw rod; wherein the propulsion driving motor is fixed on the bracket and is in driving connection with the screw rod to drive the screw rod to rotate; wherein the sliding seat is slidably disposed in the pump body along an axial direction of the syringe; wherein the half nut is slidably disposed on the sliding seat with a sliding direction perpendicular to the axial direction of the screw rod; wherein the clutch driving assembly is disposed on the sliding seat and is in driving connection with the half nut to drive the half nut to slide reciprocally, whereby the half nut is close to or away from the screw rod repeatedly;
wherein the propulsion mechanism comprises a connecting rod, a pushing block, a pressure sensing assembly, and a clutch switch; wherein the connecting rod is axially in parallel with the syringe, and the connecting rod is slidably connected to the pump body along an axial direction of the connecting rod; wherein the connecting rod has a first end fixedly connected to the pushing block and a second end fixedly connected to the sliding seat; wherein the pressure sensing assembly is disposed on the pushing block, to abut against a piston rod of the syringe to detect pressure of the piston rod, and the pressure sensing assembly is electrically connected to the control system; wherein the clutch switch is disposed on the pushing block and electrically connected to the clutch driving assembly to control operation of the clutch driving assembly; and
wherein the propulsion driving motor and the clutch driving assembly are both electrically connected to the control system to enable the manual operation mode or the electric operation mode under control of the control system;
wherein the pressure sensing assembly comprises a pressure sensor, a sliding column, and an elastic member;
wherein the pressure sensor is fixed in the pushing block; wherein the sliding column is axially in parallel with the syringe, the sliding column is slidably connected to the pushing block along an axial direction of the sliding column, and the sliding column has a first end configured to abut against the piston rod of the syringe and a second end configured to abut against the pressure sensor; wherein the elastic member is arranged between the sliding column and the pushing block; and
wherein the second end of the sliding column is configured to abut against the pressure sensor, and the elastic member is configured to deform and apply a force to the sliding column to make the sliding column move towards the syringe, when the first end of the sliding column abuts against the piston rod of the syringe; wherein the sliding column is configured to move towards the syringe under the force applied by the elastic member, and the second end of the sliding column is configured to be separated from the pressure sensor, when the first end of the sliding column is separated from the piston rod of the syringe.

14. A syringe pump, being operable in a manual operation mode and an electric operation mode, comprising:
a pump body configured to mount a syringe;
a control system;
a transmission mechanism; and
a propulsion mechanism;
wherein the transmission mechanism comprises a bracket, a propulsion driving motor, a screw rod, a sliding seat, a half nut, and a clutch driving assembly; wherein the bracket is fixed in the pump body, the screw rod is axially in parallel with the syringe, and the screw rod is rotatably connected to the bracket along an axial direction of the screw rod; wherein the propulsion driving motor is fixed on the bracket and is in driving connection with the screw rod to drive the screw rod to rotate; wherein the sliding seat is slidably disposed in the pump body along an axial direction of the syringe; wherein the half nut is slidably disposed on the sliding seat with a sliding direction perpendicular to the axial direction of the screw rod; wherein the clutch driving assembly is disposed on the sliding seat and is in driving connection with the half nut to drive the half nut to slide reciprocally, whereby the half nut is close to or away from the screw rod repeatedly;
wherein the propulsion mechanism comprises a connecting rod, a pushing block, a pressure sensing assembly, and a clutch switch; wherein the connecting rod is axially in parallel with the syringe, and the connecting rod is slidably connected to the pump body along an axial direction of the connecting rod; wherein the connecting rod has a first end fixedly connected to the pushing block and a second end fixedly connected to the sliding seat; wherein the pressure sensing assembly is disposed on the pushing block, to abut against a piston rod of the syringe to detect pressure of the piston rod, and the pressure sensing assembly is electrically connected to the control system; wherein the clutch switch is disposed on the pushing block and electrically connected to the clutch driving assembly to control operation of the clutch driving assembly; and
wherein the propulsion driving motor and the clutch driving assembly are both electrically connected to the control system to enable the manual operation mode or the electric operation mode under control of the control system;
wherein the propulsion mechanism further comprises a clamping assembly configured to release or clamp the piston rod of the syringe, the clamping assembly comprising a first claw and a second claw disposed symmetrically and comprising a clamping driving motor; wherein each claw is rotatably coupled to the pushing block, and disposed on a side surface of the pushing block towards the syringe; wherein each claw is provided with a gear, and the two gears are engaged with each other; wherein the clamping driving motor is in driving connection with the first claw to drive the first claw to rotate, whereby the two claws are far away from or close to each other; and wherein the clamping driving motor is electrically connected to the control system to operate under the control of the control system.

* * * * *